United States Patent [19]
Samson

[11] Patent Number: 6,053,903
[45] Date of Patent: Apr. 25, 2000

[54] HIGH PERFORMANCE SPIRAL-WOUND CATHETER

[75] Inventor: Gene Samson, Milpitas, Calif.

[73] Assignee: Target Therapeutics, Inc., Fremont, Calif.

[21] Appl. No.: 09/167,396

[22] Filed: Oct. 6, 1998

Related U.S. Application Data

[63] Continuation of application No. 08/868,036, Jun. 3, 1997, Pat. No. 5,853,400, which is a continuation of application No. 08/338,018, Nov. 10, 1994, Pat. No. 5,658,264.

[51] Int. Cl.$^7$ .................................................. A61M 25/00
[52] U.S. Cl. ........................... 604/526; 604/523; 604/524
[58] Field of Search ............................ 604/282, 95, 264, 604/280, 281, 523, 524, 526, 525, 527; 264/241, 249, 258

[56] References Cited

U.S. PATENT DOCUMENTS

3,757,768  9/1973  Kline ........................................ 600/434
5,395,334  3/1995  Keith et al. ............................... 604/102

*Primary Examiner*—Ronald Stright
*Assistant Examiner*—Kent Gring
*Attorney, Agent, or Firm*—Morrison & Foerster LLP

[57] ABSTRACT

This invention is a surgical device. In particular, it is a catheter suitable for accessing a tissue target within the body, typically a target which is accessible through the vascular system. Central to the invention is the use of a stiffener ribbon, typically metallic, wound within the catheter body in such a way as to create a catheter having controllable stiffness. The stiffener ribbon is adhesively bonded to a flexible outer tubing member so to produce a thin wall catheter section which is exceptionally flexible but highly kink resistant. The catheter sections made according to this invention may be used in conjunction with other catheter sections either using the concepts shown herein or made in other ways. Because of the effective strength and ability to retain a generally kink-free form, these catheters may be effectively used in sizes which are quite fine, e.g., 0.015" to 0.020" in diameter, and usable within typical vascular catheters.

24 Claims, 5 Drawing Sheets

HIGH PERFORMANCE SPIRAL-WOUND CATHETER

This application is a continuation of U.S. Ser. No. 08/868,036, filed Jun. 3, 1997, now U.S. Pat. No. 5,853,400 which is a continuation of U.S. Ser. No. 08/338,018, filed Nov. 10, 1994, now U.S. Pat. No. 5,658,264.

FIELD OF THE INVENTION

This invention is a surgical device. In particular, it is a catheter suitable for accessing a tissue target within the body, typically a target which is accessible through the vascular system. Central to the invention is the use of a stiffener ribbon, typically metallic, wound within the catheter body in such a way to create a catheter having an exceptionally thin wall and controlled stiffness. The stiffener ribbon is adhesively bonded to a flexible outer tubing member so to produce a catheter section which is very flexible but highly kink resistant.

The catheter sections made according to this invention may be used in conjunction with other catheter sections either using the concepts shown herein or made in other ways. Because of the effective strength and ability to retain a generally kink-free form, these catheters may be effectively used in sizes which are quite fine, e.g., 0.015" to 0.020" in diameter, and usable within typical vascular catheters.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of diseases of the circulatory system is via angioplasty (PCTA). Such a procedure uses catheters having balloons on their distal tips. It is similarly common that those catheters are used to deliver a radiopaque agent to the site in question prior to the PCTA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered.

This invention is an adaptable one and may be used in a variety of catheter formats. The invention utilizes the concept of adhesively combining one or more polymeric tubes with one or more spirally wound ribbons (each wound in the same direction) to control the stiffness of the resultant catheter section or body. The construction technique allows the production of catheter sections having very small diameters—diameters so small that the secondary catheters may be used interior to other vascular catheters, with or without guidewires. This catheter may be used in conjunction with a guidewire, but the catheter body may also be used as a flow-directed catheter with the attachment of a balloon or in combination with a specifically flexible tip, as is seen, for instance, in U.S. Pat. No. 5,336,205 to Zenzen et al., the entirety of which is incorporated by reference.

The use of ribbons in winding a catheter body is not a novel concept. Typical background patents are discussed below. However, none of these documents have used my concept to produce a catheter which has the physical capabilities of the catheter of this invention.

Multi-Wrap Catheters

There are a number of catheters discussed in the literature which utilize catheter bodies having multiply wrapped reinforcing material. These catheters include structures having braided bands or ones in which the spirally wound material is simply wound in one direction and the following layer or layers are wound in the other.

Crippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in some region other than in the body's periphery or in its soft tissues.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands-which are braided, that is to say, bands which are spiralled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above. No suggestion is made that any of these multiple layers be simplified into a single, spirally-wrapped layer adhesively bound to an outer polymeric covering.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

Single-Layer, Reinforced Catheters

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to de Toledo, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,567,024, to Coneys, shows a catheter which employs a set of helical strips within the wall of the catheter. However, the helical strips are of a radiopaque material, e.g., fluorinated ethylenepropylene. It is not clear that the blended radiopaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube. There is no suggestion within the patent that the interior coil be made to adhere to the outer tubular sheath.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy". There is no suggestion of utilizing an adhesive to bond the interior wire to the exterior tubing. The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end. There is no suggestion that the wire forming the helical core be adhesively attached to its outer coverings.

U.S. Pat. No. 5,313,967, to Lieber et al., shows a medical device a portion of which is a helical coil which, apparently, may include an outer plastic sheath in some variations. Apparently, a secondary helix of a somewhat similar design, in that it is formed by rotating a flat wire or the like along its longitudinal axis to form a screw-like configuration, is included within the helical coil to provide axial pushability and torque transmission.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold." The document does not suggest that the coil be made to adhere to the outer polymeric jacket using an adhesive.

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultrathin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermoplastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . . ". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described. No suggestion of the use of an adhesive is made in the patent.

European Pat. Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Patent Document 2,613,231, describes a medical probe used with an endoscope or for some other device used to stimulate the heart. The device appears to be a helix having a spacing between 0 and 0.25 mm (See page 4, line 20) preferably rectangular in cross section (See Page 4, Line 1) and of a multi-phase alloy such as M35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-Kinking Configurations

U.S. Pat. No. 5,222,949, to Kaldany, describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher integral of cross-linking.

European Patent Application No. 0,421,650-A1 describes a method for producing a catheter from a roll of polymer film while incorporating other materials such as tinfoil elements or the like.

None of the documents cited above provides a structure required by the disclosure and claims recited below, particularly when the flexibility and ability to resist kinks is factored into the physical description of the devices.

SUMMARY OF THE INVENTION

This invention is a catheter section made up of one or more spirally wound stiffener ribbons adhesively attached to an outer polymeric covering.

The stiffener ribbon is, in its most basic form, a single strand of ribbon wound in a single direction. A number of ribbons of the same or differing sizes and compositions may also be used, but such ribbons are wound the same direction to form a single layer of ribbon and form a lumen from the distal to the proximal end of the catheter section. The ribbons are typically metallic but may be of other materials. I have found that a necessary portion of the invention is the requirement that the ribbons adhere to the outer covering. In this way, the kink resistance of the catheter section is established due to the lack of slippage between the cover and the spiral coil. The outer cover, in the regions between coil turns, retains a high level of patency. The absence of slippage prevents the formation of localized areas of larger spacing between coil turns and the resulting source of kinking sites.

The catheter sections of this invention may be formed into an integral catheter assembly. Wise choices of materials permit the catheter to be of a smaller overall diameter with a superior critical diameter. Indeed, one variation of this invention involves telescoping catheters with an inner catheter of this construction, perhaps with an inner guidewire. The catheter may be designed to integrate lubricious materials into the base design of a particular catheter product without adding extraneous thickness and stiffness. The catheter may be wholly constructed of materials which are stable to radioactive sterilization procedures.

DESCRIPTION OF THE INVENTION

This invention is a kink-resistant catheter section or a catheter. If a catheter, it is a composite device having at least one section including at least one helically wound ribbon stiffener coaxial to and adhesively attached to at least one polymeric outer section. The ribbon forms the inner lumen of the catheter section. The catheter is configured so that at least the distal portion of the catheter has a critical bend diameter of no more than 3.5 mm, preferably no more than 2.5 mm, more preferably no more than 1.5 mm, and most preferably no more than 1.0 mm. I have additionally found that the radial compression strength of the section is quite high as compared to distal sections found on comparable catheters.

Figure 1:
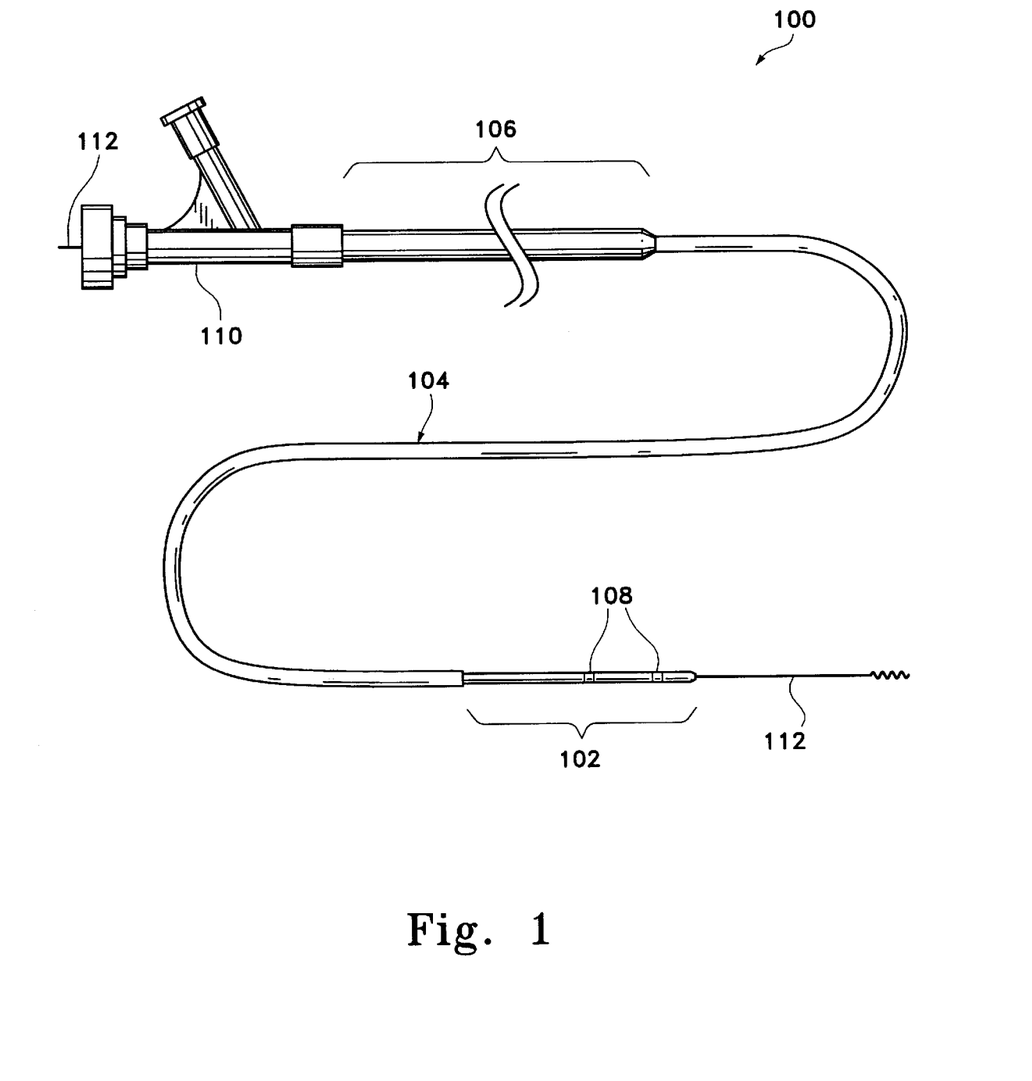
FIG. 1 shows, in side view, a typical three section catheter.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever more smaller vascular areas. This smaller diameter requires a concomitant thinning of the wall section. The thinner section walls may kink or ripple when actively pushed along the guidewire or when vasoocclusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration of the extraordinary convolutions of the neurological vasculature without trauma. Various known and often necessary accessories to the catheter assembly, e.g., one or more radiopaque bands (108) at the distal region to allow viewing of the position of the distal region under fluoroscopy and a luer assembly (110) for guidewire (112) and fluids access, are also shown in FIG. 1. The typical dimensions of this catheter are:

Overall length: 60–200 cm

Proximal Section (106): 60–150 cm

Intermediate Section (104): 20–50 cm

Distal Section (102): 2.5–30 cm

Obviously, these dimensions are not particularly critical to this invention and are selected as a function of the malady treated and its site within the body. However, as will be discussed below, use of the spiral wound ribbon permits the walls of the catheter to be somewhat thinner with no diminution of performance, e.g., crush strength or flexibility, and, indeed, usually provides an improvement in performance.

Figure 2:
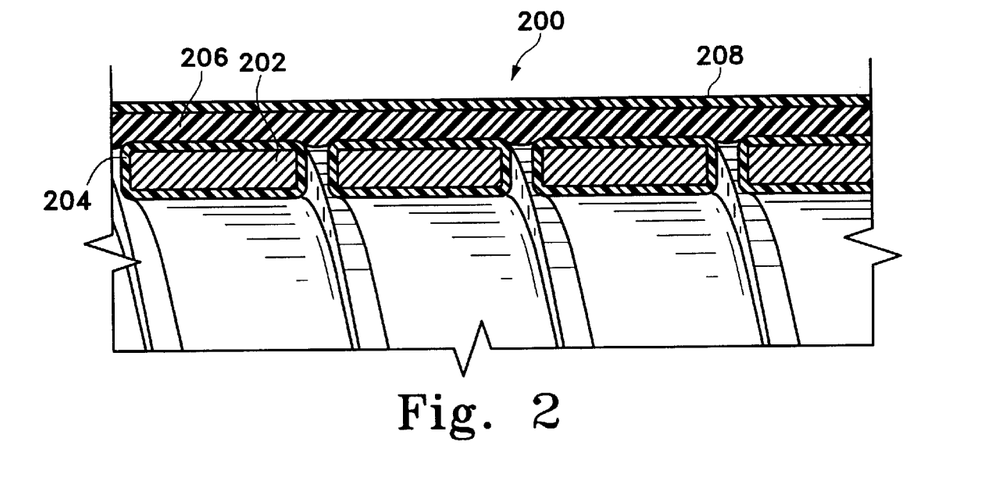
FIG. 2 shows, in magnification, a section of the inner portion of one inventive section of this catheter.

FIG. 2 shows a magnified cross-section of a catheter body or section (200) showing the most basic aspects of one variation of the invention. As shown there, the catheter body or section has a helically wound ribbon (202) and an adhesive (204) on at least an outer portion of the ribbon (202). Typically, the outer tubing member (206) is polymeric. Preferably, the outer tubing member (206) is, produced of a polymer which is heat shrinkable onto the adhesive (204). Such polymers include known materials such as polyethylene, polyvinylchloride (PVC), ethylvinylacetate (EVA), polyethylene terephalate (PET), and their mixtures and copolymers. One very useful class of polymers are the thermoplastic elastomers, particularly polyesters. Typical of this class is HYTREL. Similarly, the adhesive (204) is desirably a thermoplastic which may be coated onto the inner lumen of the outer tubing member (206), the outer surface of the coil (as wound), the ribbon itself, or may be formed in situ by the use of a mixture of polymers such as polyethylene and EVA, which when heated to a proper temperature exude the EVA onto the ribbon. A very highly desirable combination—from an assembly point of view—is the use of an thermoplastic adhesive (204) having a softening temperature between the temperature for heat shrinking the outer tubing (206) onto the adhesive (204) and the melting temperature of that outer tubing (206).

I have found that an outer covering of EVA having a suitable softening/heat shrinking temperature is an excellent choice for securing a strong bond to the ribbon particularly with an adhesive such as polyester or polyimide. The EVA (obviously, with or without other mixed polymers and fillers) is typically extruded into a taking of an appropriate size and thickness and cross-linked to raise the melt temperature of the resultant tubing. The tubing is then inflated and, perhaps, stretched to give the included polymer molecular orientation. The tubing may then be heat-shrunk onto the catheter. A suitable EVA would have significant adhesive properties at about 300° F.

This is not to exclude the use of other polymers, depending on the section of the catheter in which the section is used. For instance, the tubing may be of any of a variety of polymers, variously stiff or flexible. For instance, if the section (200) is used as a proximal section, the outer tubing member (206) may be a polyimide, polyamides such as the Nylons, high density polyethylene (HDPE), polypropylene, polyvinylchloride, various fluoropolymers (for instance: PTFE, FEP, vinylidene fluoride, mixtures, alloys, copolymers, block copolymers, etc.), polysulfones or the like. Blends, alloys, mixtures, copolymers, block copolymers, of these materials are also suitable, if desired.

If a more flexible section is required, the outer tubing member (206) may be a polyurethane, low density polyethylene (LDPE), polyvinylchloride, THY, etc. and other polymers of suitable softness or modulus of elasticity.

Although it is quite difficult to accomplish, the inventive catheter design allows the use in the distal portion of the catheter, thin-walled tubing of inherently more slippery polymers, such as PTFE and FEP and their mixtures, which have the benefit of being lubricious but otherwise would have been used in a somewhat greater thickness. Production of a good adhesive joint between the helically wound ribbon (202) and the adhesive (204) is not an easy task. Clearly, greater thickness tubing of these polymers results in the resulting catheter section being somewhat stiffer. The wall thickness of the outer tubing member (206) may be as thin as 0.5 mil and as thick as 10 mil, depending upon catheter usage, portion of the catheter chosen, polymer choice, and the style of catheter.

Typically, the wall thickness of the tubing member will be between 0.5 and 3.0 mils. This dimension is obviously only a range and each catheter variation must be carefully designed for the specific purpose to which it is placed.

Preferred combinations of polymers for catheter configurations will also be discussed below. It should also be noted at this point that each of the polymers discussed herein may be used in conjunction with radiopaque material such as barium sulfate, bismuth trioxide, bismuth carbonate, powdered tungsten, powdered tantalum, or the like so that the location of the various pieces of tubing may be radiographically visualized within the vessel.

The spiral wound ribbon (202) shown in FIG. 2 may also be of a variety of different materials. Although metallic ribbons are preferred because of their strength-to-weight ratios, fibrous materials (both synthetic and natural) may also be used. Preferred, because of cost, strength, and ready availability are stainless steels (SS308, SS304, SS318, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radiopacity.

The class of alloys known as super-elastic alloys is also a desirable selection. Preferred super-elastic alloys include the class of titanium/nickel materials known as nitinol—alloys discovered by the U.S. Navy Ordnance Laboratory. These materials are discussed at length in U.S. Pat. No. 3,174,851 to Buehler et al., U.S. Pat. No. 3,351,463 to Rozner et al., and U.S. Pat. No. 3,753,700 to Harrison et al. These alloys are not readily commercially available in the small ribbons required by the invention described here, but for very high performance catheters are excellent choices.

When using a superelastic alloy, an additional step is usually necessary to preserve the helical shape of the stiffening member. I have purchased nitinol wire and rolled it into a 1×4 mil ribbon. The ribbon is then helically wound onto a mandrel, usually metallic, of an appropriate size. The winding is then heated to a temperature of 650°–750° F. for a few minutes, presumably annealing the ribbon. The helical coil then retains its shape.

Metallic ribbons (202) that are suitable for use in this invention are desirably between 0.5 mil and 1.5 mil in thickness and 2.5 mil and 8.0 mil in width. By the term "ribbon", I intend to include elongated shapes, the cross-section of which are not square or round and may typically be rectangular, oval or semi-oval. They should have an aspect ratio of at least 0.5 (thickness/width). In any event, for superelastic alloys, particularly nitinol, the thickness and width may be somewhat finer, e.g., down to 0.30 mil and 1.0 mil, respectively. Currently available stainless steel ribbons include sizes of 1 mil×3 mil, 2 mil×6 mil, and 2 mil×8 mil.

Suitable non-metallic ribbons include high performance materials such as those made of polyaramids (e.g., KEVLAR) and carbon fibers.

It should be observed that the preferred manner of using non-metallic ribbons in this invention is typically in combination with metallic ribbons to allow "tuning" of the stiffness of the resulting composite.

Finally, in FIG. 2 may be seen an outer layer (208) of a lubricious material such as a silicone or other, perhaps hydrophilic, material such as a polyvinylpyrrolidone composition. These compositions are well known and do not form a critical portion of the invention.

Typical of the catheter made using this invention are those in the 3 French to 5 French range. The inner diameter of such catheters is then 20 mils to 42 mils. However, I have made micro-catheters (discussed in more detail below) having outside diameters of 18 mils to 34 mils. The inner diameter of those catheters was 11 mils to 20 mils. The invention is not limited to such sizes, however.

Figure 3:
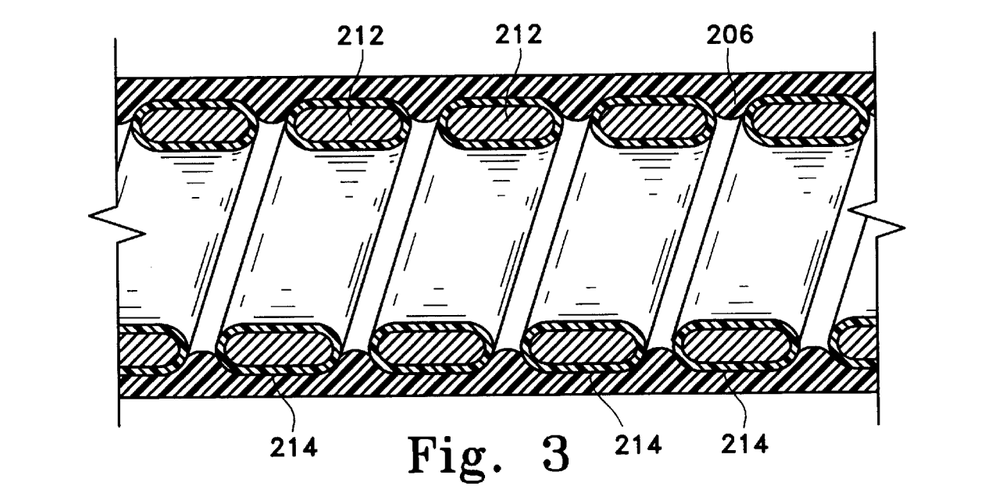
FIG. 3 shows, in magnification and cross-section, a variation of the invention using two ribbons.

FIG. 3 shows a variation of the inventive catheter (210) in which the cross-sections of the ribbons (212 & 214) are generally oval rather than rectangular than as shown in FIG. 2. Either cross-section is acceptable but the oval section has less of a tendency to bind with guidewires passing through the lumen. Additionally, the FIG. 3 variation shows the use of two ribbons (212 & 214) wound side-by-side so to form a single layer of ribbon inside the outer tubing cover (206). The dual ribbons may be of the same composition or of differing compositions. They may be of the same size or of differing sizes. The number of ribbons may be of any convenient configuration so long as the specific stiffness and kink-resisting criteria are met.

Figure 4:
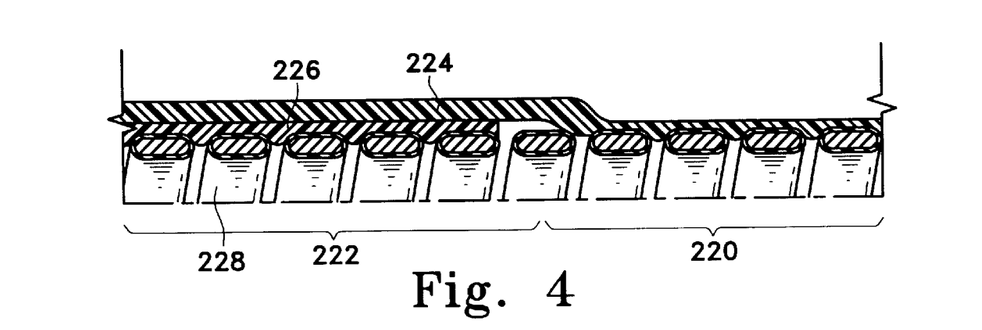
FIG. 4 shows, in magnified fractional view, a multisection catheter assembly.
Figure 5:
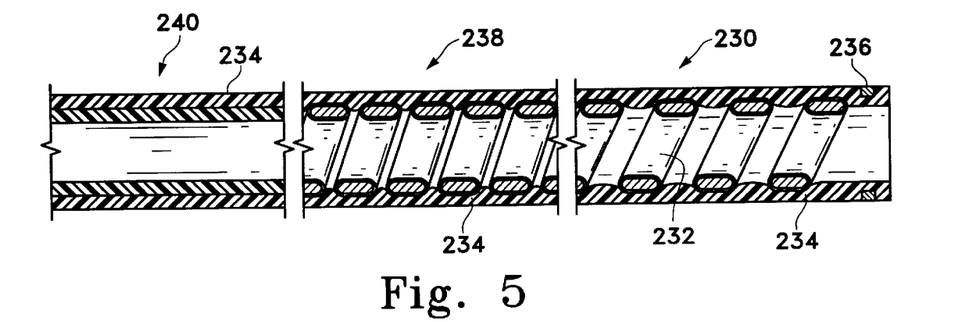
FIGS. 5–8 show, in magnified cross-section, various catheters having sections of differing stiffness.
Figure 6:
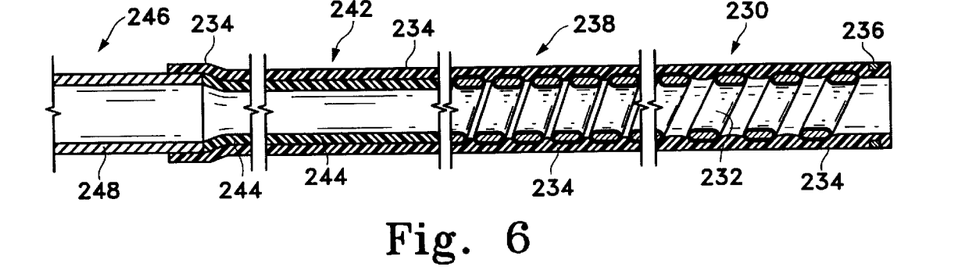
Figure 7:
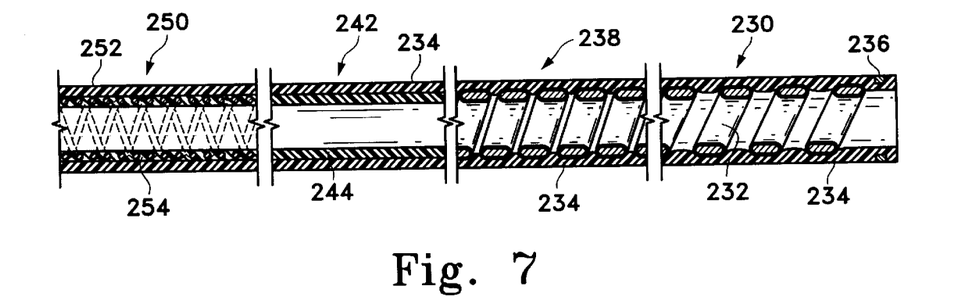

FIG. 4 shows another variation in which catheter sections made according to this invention are used in axial conjunction. Section (220) is generally as described in FIGS. 3 and 4 above, but section (222) is more proximal and enjoys two outer covering layers (224) and (226). Covering (224) is simply a proximal extension of the polymeric covering in section (220); polymeric covering (226) is placed directly on the outer surface of the helically-wound coil (228). As has been noted elsewhere, coil (228) may be the same as or different than the coil found in the more distal section (220). Other methods for changing the stiffness of various sections of a catheter made using sections of the inventive catheter section are shown in FIGS. 5, 6, and 7. For instance, FIG. 5 shows a distal section (230) having a helically-wound ribbon (232), an outer polymeric covering (234), and a radiopaque band (236). In this variation, the ribbon (232) is wound in such a fashion that adjacent turns are not contiguous. This allows the distal catheter section (230) to be quite flexible and kink-resistant. The intermediate section (238) retains the same outer covering (234), but the pitch of the coil has been narrowed so that the flexibility of the midsection (238) is not as high as was the distal section (230).

The most proximal section (240) has no helically-wound ribbon at all, but instead uses a variety of polymeric or other tubing materials to form the stiffest portion of the catheter assembly. In this instance, the outer layer remains as found in the most distal section (230) and the midsection (238). The inner layer in this instance is a stiffer material, such as polyimide, polypropylene, or a stainless steel tube, known as a "hypotube".

FIG. 6 shows still another variation of forming the distal section of a catheter assembly which is flexible and yet provides a greater stiffness for other sections of the catheter assembly. For instance, in FIG. 6, the intermediate section (242) utilizes double layers of polymeric material, e.g., the outer tubing (234) (discussed above) on the outer surface and an inner tubing of similar or stiffer material (244) in contiguous relationship along the length of the section (242). The most proximal section (246) shows only a short overlap between stiff distal tube (248) (perhaps made of the polyimide, polypropylene, nylon, or hypotube materials discussed above) and the outer layer (234). This is a simple arrangement and may be used, for instance, where cost is at a premium.

Figure 8:
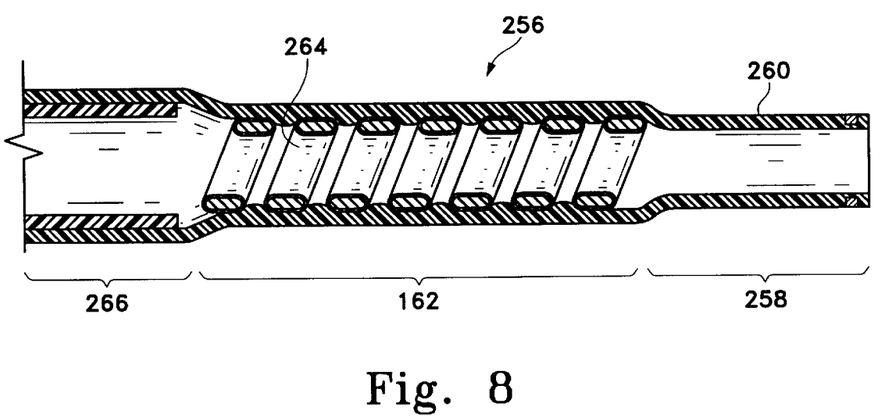

FIG. 7 shows still a further variation in which the most distal section is a composite of polymeric layers (252) and a braid (254). The composition of the mid and proximal sections are not critical to the invention. They may be of one type or the other depending upon the requirements of the particular application. The most significant of benefits is accrued when, however, the distal section is of the type specified herein. Nevertheless, a variation shown in FIG. 8 depicts an instance in which the non-kinking criteria of this invention is applied in a mid-section. Catheter (256) uses a distal section having only tubing (260) extending distally of the mid-section (262). Mid-section (262) comprises both outer tubing (260) and helically-wound ribbon (264) easily held in place according to this invention. Proximal section (266) is made stiffer by incorporating multiple layers of tubing, as discussed above.

Although the exemplified catheter assemblies in FIGS. 1, 5, 6, 7, and 8 each utilize three sections, it should be understood that this invention is not so limited. The number of sections is selected by the designer when conceptualizing a specific use for a chosen device. Often, the optimum number of sections ends up being three simply because of the physiology of the human body, however, three or more may be involved in this invention. The sections additionally need not be of constant stiffness. They may also vary in stiffness—typically as the distal end of a section is approached, the section becomes more flexible.

Figure 9:
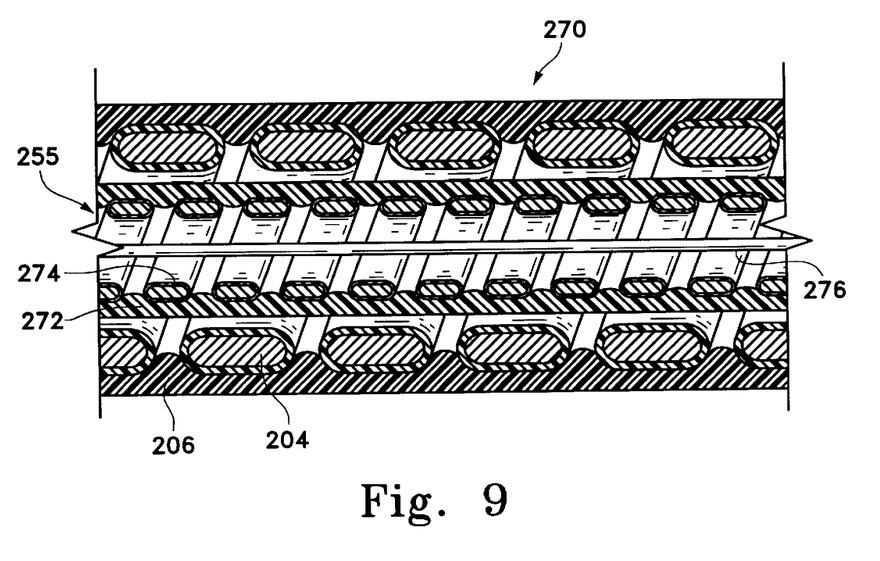
FIG. 9 shows, in cross-section, a combination of outer and inner catheter sections made according to the invention and an inner guidewire, all in slidable relationship to each other.

As was noted above, I have found that use of this method of construction allows use of significantly smaller diameter catheters which still remain kink-free and yet are quite useable. For instance, FIG. 9 shows a short cross-section of a distal end of a vascular catheter (270) in which the outer section comprises an outer cover (206) and a helically-wound ribbon (204) generally as shown in FIG. 2. Within the lumen defined by a helically-wound coil (204) may be found yet a smaller catheter device covering (272) and a helically-wound coil (274). Again, it is desireable that helically-wound coil (274) and covering (272) be adhesively attached to each other to lessen the chance of any kinking taking place. Within the lumen of the inner catheter is a guidewire (276) which, just as an inner catheter (275), is slidable within outer catheter (270), is slidable within the inner catheter (275). For instance, a guidewire (276) may have an outside diameter of 5 to 7 mils in this distal region and the outer diameter of inner catheter (275) may have an outer diameter of 12½ to 14 mils.

As was noted above, the most distal portion of the distal section of this catheter (and preferably other sections as well) have a critical bend diameter of no more than 3.5 mm, preferably no more than 2.5 mm, more preferably no more than 1.5 mm, and most preferably no more than 1.0 mm. To some extent, the critical band diameter is also dependent upon the diameter of the catheter section and its components. For instance, I have made 3 French catheter section of the type shown in FIG. 2 (of stainless steel ribbon) with critical bond diameters less than 2.5 mm. Similarly, I have made catheter sections such as the inner catheter (275) shown in FIG. 9 with an outer diameter of 0.018" (of platinum-tungsten alloy ribbon) with band diameters less than 1.0 mm.

Figure 10A:
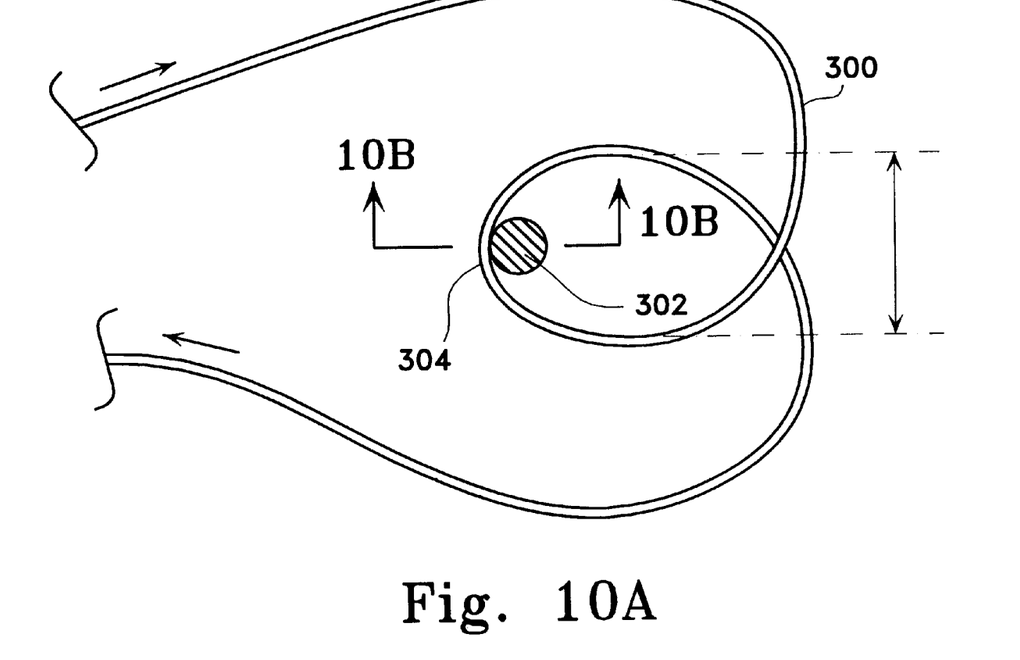
FIGS. 10A and 10B show details of methods for determining the "critical bend diameter" for a catheter.
Figure 10B:
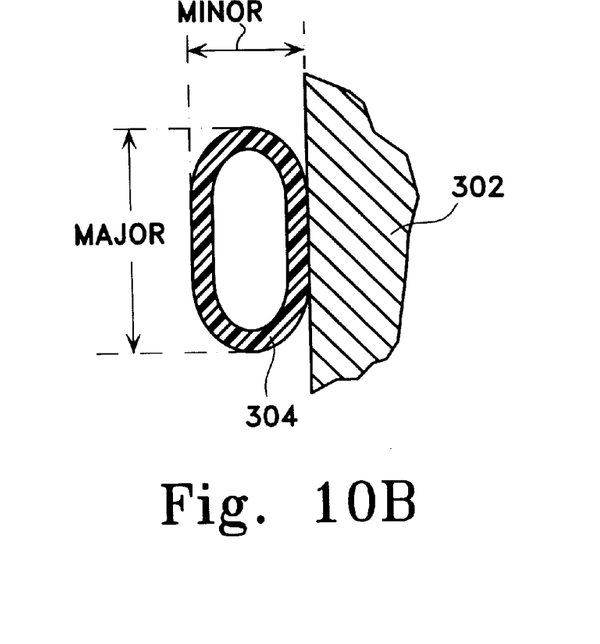

The test we utilize for critical bend diameter determination uses a test shown schematically in FIGS. 10A and 10B.

In general, as shown in FIG. 10A, a catheter section (300) is placed between two plates (desirably of plastic or glass or the like for visibility) and often with an optional peg (302) to hold the catheter section (300) loop in place. The ends of the catheter are then pulled until a kink appears in the body of the catheter. Alternatively, the ratio of the outer diameters (major diameter:minor diameter) as measured at apex (304) reaches a value of 1.5. FIG. 10B shows the cross section of the catheter sector at (304) and further shows the manner in which the major diameter and the minor diameter are measured. These two methods provide comparable results although the latter method is more repeatable.

Many times herein, we refer to the "region" section of the catheter. Where the context permits, by "region" we mean within 15% of the point specified. For instance, "the distal region of the distal section" would refer to the most distal 15% in length of the distal section.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

I claim as my invention:

1. A catheter section comprising:
   an elongate tubular member having a proximal end and a distal end and a passageway defining an inner lumen extending between those ends, comprising
   a.) a first ribbon stiffener having a width and thickness, and said first ribbon stiffener is spirally wound with a handedness to form said passageway and an outer stiffener surface and wherein said outer stiffener surface is at least partially coated with an adhesive material, said first ribbon stiffener comprising at least one metallic ribbon and at least one nonmetallic ribbon, and
   b.) at least one tubing member exterior to and contiguous with and adherent to said first ribbon stiffener via said adhesive material.

2. The catheter section of claim 1 wherein the catheter section has a critical bend diameter of no more than 3.5 mm.

3. The catheter section of claim 1 wherein the metallic ribbon is nitinol.

4. The catheter section of claim 1 wherein the metallic ribbon is a platinum-tungsten alloy.

5. The catheter section of claim 1 additionally comprising at least a second ribbon stiffener of the same handedness coaxially wound between the spiral turns of the first ribbon stiffener.

6. The catheter section of claim 5 where the second ribbon stiffener comprises a ribbon having a thickness between 0.75 mil and 2.5 mils and a width between 2.5 and 8.0 mils.

7. The catheter section of claim 1 where the elongate tubular member has at least one region of variable stiffness between the proximal end and the distal end.

8. The catheter section of claim 1 where the first ribbon stiffener has a pitch which varies between the proximal end and distal end.

9. The catheter section of claim 1 where the first ribbon stiffener comprises a ribbon having a thickness between 0.5 mil and 2.5 mil and a width between 2.5 and 8.0 mil.

10. The catheter section of claim 1 wherein the tubing member comprises a polymer.

11. The catheter section of claim 10 wherein the tubing member comprises a polymer which can be heat-shrunk onto said first ribbon stiffener.

12. The catheter section of claim 11 wherein the tubing member comprises a polymer selected from polyethylene, ethylvinylacetate, polyethylene terephalate, polyvinylchloride, and their mixtures and copolymers.

13. The catheter section of claim 11 wherein the adhesive material has a softening temperature higher than the heat shrink temperature of the tubing member but lower than the melting temperature of the tubing member.

14. The catheter of claim 1 wherein adjacent turns in the first ribbon stiffener are contiguous.

15. The catheter of claim 1 wherein adjacent turns in the first ribbon stiffener are not contiguous.

16. The catheter section of claim 1 further comprising a second cover exterior to the tubing member.

17. The catheter section of claim 16 where the second cover comprises a material selected from polyimide, polyamides, polyethylene, polypropylene, polyvinylchloride, polyurethane, fluoropolymers including PTFE, FEP, vinylidene fluoride, and their mixtures, alloys, copolymers, and block copolymers, polysulfones or the like.

18. A catheter comprising:
   an elongate tubular member having a proximal end and a distal end and a passageway defining an inner lumen extending between those ends,
   said elongate tubular member having:
   a.) a relatively stiff proximal segment, and
   b.) a relatively flexible distal segment, said distal segment comprising
      i.) a first ribbon stiffener having a width and thickness, and said first ribbon stiffener is spirally wound with a handedness to form said passageway and an outer stiffener surface and wherein said outer stiffener surface is at least partially coated with an adhesive material, said first ribbon stiffener comprising at least one metallic ribbon and at least one nonmetallic ribbon, and
      ii.) at least one tubing member exterior to and contiguous with and adherent to said first ribbon stiffener via said adhesive material.

19. The catheter of claim 18 wherein the distal segment section has a critical bend diameter of no more than 3.5 mm.

20. The catheter of claim 18 where the proximal segment is composed of a second cover comprising a proximal cover material, said second cover exterior to a proximal extension of the tubing member and said first ribbon stiffener.

21. The catheter of claim 18 further comprising at least one intermediate segment having a flexibility intermediate the flexibility of the distal and proximal segments, said intermediate segment defining a passageway between the relatively stiff proximal segment and the relatively flexible distal segment.

22. The catheter of claim 18 where the proximal section of the catheter additionally comprises a second ribbon stiffener of the same handedness coaxially wound between the spiral turns of the first ribbon stiffener.

23. The catheter of claim 21 where the intermediate section of the catheter additionally comprises a second ribbon stiffener of the same handedness coaxially wound between the spiral turns of the first ribbon stiffener.

24. The catheter of claim 21 where the proximal section of the catheter comprises a polymeric tube proximally abutting the tubing member and said first ribbon stiffener.

\* \* \* \* \*